(12) United States Patent
Birkenstock et al.

(10) Patent No.: US 7,954,353 B2
(45) Date of Patent: Jun. 7, 2011

(54) METHOD AND DEVICE FOR TESTING THE QUALITY OF A METALLIC COATING

(75) Inventors: Andreas Birkenstock, Velbert (DE); Peter Heidbüchel, Sonsbeck (DE); Michael Linnepe, Bönen (DE)

(73) Assignee: ThyssenKrupp Steel AG, Duisburg (DE)

( * ) Notice: Subject to any disclaimer, the term of this patent is extended or adjusted under 35 U.S.C. 154(b) by 0 days.

(21) Appl. No.: 12/281,070

(22) PCT Filed: Feb. 23, 2007

(86) PCT No.: PCT/EP2007/051779
§ 371 (c)(1),
(2), (4) Date: Dec. 22, 2008

(87) PCT Pub. No.: WO2007/101795
PCT Pub. Date: Sep. 13, 2007

(65) Prior Publication Data
US 2009/0188294 A1 Jul. 30, 2009

(30) Foreign Application Priority Data

Mar. 3, 2006 (DE) .......................... 10 2006 010 431

(51) Int. Cl.
*B21D 22/00* (2006.01)
*B21B 37/16* (2006.01)
*B21C 51/00* (2006.01)
(52) U.S. Cl. ................. 72/347; 72/17.3; 72/37
(58) Field of Classification Search .......... 72/16.2–16.3, 72/17.3, 37, 350, 274, 347
See application file for complete search history.

(56) References Cited

U.S. PATENT DOCUMENTS 3,344,646 A * 10/1967 Moller ........................... 72/348
(Continued)

FOREIGN PATENT DOCUMENTS

AT 26343 11/1905
(Continued)

OTHER PUBLICATIONS

M. Golle et al.: "Der Einfluss des Vorformens auf schwach Konturierte Bauteile" [Online] 2001, XP002431278 Gefunden im Internet: URL:http://www.lfu.mb.uni-dortmund.de/page s/de/content/projekte/foerderung/spp1098/07_der_einfluss_des_vorformens_auf_schwach_konturierte_bauteile_2001.pdf> [gefunden am Apr. 26, 2007].

(Continued)

*Primary Examiner* — Dana Ross
*Assistant Examiner* — Mohammad Yusuf
(74) *Attorney, Agent, or Firm* — Proskauer Rose LLP

(57) ABSTRACT

A method and a device for determining a quality of a metallic surface of a metallic substrate, for example a steel or steel alloy substrate, are provided. The device includes a mould, a sheet holder and a die, with which the metallic substrate is formed to produce a drawn test surface. The method and device are used to test the quality of the metallic surface of a metallic coating with a view to a later utilization, especially with a view to a later forming, wherein the metallic substrate is formed at least in-an area of a test surface, wherein a main and an additional shape change of the metallic substrate in the area of the test surface assume predetermined values that are related to the later utilization of the metallic substrate, and wherein the quality of the metallic surface is tested on the test surface after forming.

9 Claims, 2 Drawing Sheets

U.S. PATENT DOCUMENTS

| | | | | | |
|---|---|---|---|---|---|
| 3,928,901 | A | * | 12/1975 | Schilling et al. | 72/56 |
| 4,562,715 | A | * | 1/1986 | Brun et al. | 72/347 |
| 4,663,956 | A | * | 5/1987 | Brun et al. | 72/347 |
| 4,920,385 | A | * | 4/1990 | Clarke et al. | 356/237.2 |
| 5,448,902 | A | * | 9/1995 | Thoms et al. | 72/350 |
| 5,532,051 | A | * | 7/1996 | Nishiura et al. | 72/353.6 |
| 5,901,599 | A | | 5/1999 | Sato et al. | 72/350 |
| 6,033,499 | A | | 3/2000 | Mitra | 148/688 |
| 6,722,009 | B2 | * | 4/2004 | Kojima et al. | 29/421.1 |

FOREIGN PATENT DOCUMENTS

| | | |
|---|---|---|
| DE | 282 075 | 8/1990 |
| DE | 693 17 268 | 6/1998 |
| DE | 100 42 407 | 4/2002 |
| DE | 10111296 | 9/2002 |
| EP | 0754508 | 1/1997 |

OTHER PUBLICATIONS

"Blechumformung "under control"" Electro Automation, [Online] Bd. 54, Nr. 8, Aug. 2001, Seiten 66-67, XP002431279 Gefunden im Internet: URL:tyyp://www.logic-instrument.de/news/clippings/download/08-2001_ea.pdf> [gefunden am Apr. 26, 2007].

M. Merklein et al.: "Entwicklung einer neuen Analysemethode für die Charakterisierung des Formgebungsvermögens metallischer Werkstoffe" [Online] 2003, Seiten 1-5, XP002431280 Gefunden im Internet: URL:http://www.utfscience.de/pdf/27202_UT-3-01_003xx0103ut.pdf> [gefunden am Apr. 26, 2007].

International Search Report for PCT/EP2007/051779.

* cited by examiner

METHOD AND DEVICE FOR TESTING THE QUALITY OF A METALLIC COATING

CROSS-REFERENCE TO RELATED APPLICATIONS

This application is a National Phase Application of International Patent Application No. PCT/EP2007/051779, filed on Feb. 23, 2007, which claims the benefit of and priority to German Patent Application No. DE 10 2006 010 431.5-52, filed on Mar. 3, 2006, which is owned by the assignee of the instant application. The disclosure of each of these applications is incorporated herein by reference in its entirety.

FIELD OF THE INVENTION

The invention relates to a method for determining the quality of a metallic surface of a metallic substrate, for example a steel or steel alloy substrate, and to a device for determining the quality of a metallic surface of a metallic substrate, comprising a mould, a sheet holder and a die, with which the metallic substrate is formed in order to produce a drawn test surface.

BACKGROUND OF THE INVENTION

In the production of motor vehicles sheets, metallic substrates are frequently coated to achieve certain characteristics, for example good corrosion resistance. A coating is usually applied strip-wise or sheet-wise to the metallic substrate before a forming process, so that not only the metallic substrate but also its coating can have good forming characteristics. A typical example of such coating is hot-dip galvanizing of steel parts, which are used for example for the body shell of a motor car. The coating quality is therein dependent on various parameters, therefore it is desirable in the preliminary stage, i.e., before the subsequent processing of the metallic substrate for example into body parts, to test the surface quality. A similar problem also concerns uncoated sheets, for example thin sheets, since for example rolling defects frequently only appear when the thin sheet is formed into a product. In this case it is also desirable to test the surface quality, while taking the further forming of the sheet into consideration.

A plurality of methods for testing the surface finish of a metallic substrate is well-known from the art. For example, it is known from DE 101 11 296 A1 to examine the surface quality of a flat product by evaluating electronic images of the surface of the flat product. However, information about whether and for which forming processes the surface and/or the coating are suitable cannot be obtained with the known method.

SUMMARY OF THE INVENTION

In one aspect, the present invention is related to a method as well as a device for determining the quality of a metallic coating (i.e. surface) on a metallic substrate, with which the quality of the metallic coating can be tested with a view to a later utilization of the metallic substrate, especially with a view to its later forming.

In an embodiment in accordance with the present invention, a method is provided, wherein the metallic substrate is formed at least in the area of a test surface, wherein a main and an additional shape change of the metallic substrate in the area of the test surface assume predetermined values that are related to the later utilization of the metallic substrate, and wherein the quality of the metallic surface of the test surface is tested after forming.

It has been shown for example that the sheet parts used in different areas of a motor vehicle are subjected to various degrees of forming during production. For example metallic substrates for roof structures of motor vehicles are exposed to relatively small main shape changes of about 1-2%. When a sheet part for the side panel of a motor vehicle is produced typically main shape changes of about 5% occur. When parts for the bonnet of a motor vehicle are produced usually main shape changes of about 3% occur. In embodiments in accordance with the invention, the main and additional shape changes occurring during subsequent processing are now simulated in a controlled manner and, subsequently, the test surface comprising the corresponding main and additional shape changes is tested as regards the quality of the metallic surface. The metallic surface of the test surface is tested optically, for example by using a microscope or other optical and/or opto-electronic devices. In contrast to known methods, the quality of the surface is tested with a view to its utilization, i.e., for example, whether the metallic substrate can be subjected to certain forming without defects in the metallic surface arising. Thus, it is possible in principle to assign different forming requirements to the metallic substrates and minimize the rejection rate when producing structure parts for motor vehicles.

Preferably, the metallic substrate, in an embodiment in accordance with the invention, is drawn, for example, in a material-forming tool with a die, and the main shape change is adjusted via the drawing depth, so that the main shape change can be reproducibly introduced, in a simple manner, into the metallic substrate.

Determination of the quality of the metallic surface of a metallic substrate for body shell parts of motor vehicles can be achieved, wherein the main shape change of the substrate in the area of the test surface amounts to 7% maximum, which are the typical maximum values for main shape changes of body shell parts of motor vehicles during production.

If the additional shape change of the substrate in the area of the test surface amounts to between −2% and +2%, the additional shape changes also lie in a range, which is typical for a specific use. For determining the quality of the metallic surface an additional shape change of about 0% is set in order to obtain test results particularly in line with standard practice for determining the surface quality of the metallic substrate.

In another embodiment in accordance with the invention, possible defects on the surface of a metallic substrate can be relatively easily recognized due to the fact that the test surface is abraded after forming. In particular defects on the metallic surface caused by the production process can be made visible by abrading the test surface.

Preferably, sheets with a maximum thickness of 1.5 mm, preferably with a thickness from 0.3 mm to 1 mm, and a maximum strength of 500 MPa, preferably 140 to 500 MPa, are used as the metallic substrate, since these sheets have particularly good characteristics as regards their use as body shell parts in the construction of motor vehicles.

Embodiments in accordance with the invention are particularly suitable for detecting defects of metallic coatings, especially (electrolytically) zinc-plated or hot-dip galvanized coatings. Substrates coated accordingly, as already stated, are preferably used in the construction of motor vehicles for body shell parts.

In another embodiment in accordance with the present invention, a generic device is provided, wherein the die is formed in the area of the test surface of the formed substrate such that the main shape change amounts to 7% maximum and the additional shape change amounts to between −2% and +2%, preferably close to 0%. With the die formed accordingly, specific main shape changes are produced in the test surface that are related to utilization, for example as body shell part of a motor vehicle, which permits the quality of the metallic coating to be determined in line with standard practice, particularly with respect to further processing of the metallic substrate.

Preferably the die has a length of at least 400 mm and a width of at least 250 mm in order to create as large a test surface as possible. The test surface is adapted to the dimensions of the metallic substrates, which are specific for their use in the construction of motor vehicles, so that determining the quality of the metallic coating of the test surface provides a representative statement about the quality of the coating of the entire metallic substrate.

In another embodiment in accordance with the invention, the direction of the main shape change is exactly predetermined by the die previously formed in the test surface. The die has a front face with a curvature towards the main shape change with a radius of curvature from 500 to 2000 mm, preferably 1000 mm. During the forming process, particularly during the drawing process, the main shape change is exactly defined by the curvature of the front face of the die. Due to the wide radius of curvature the main shape change is effected homogeneously over the entire test surface.

If the edge radius between the front face of the die and two longitudinal side faces of the die, running transversely to the direction of the main shape change, amounts to 20 to 80 mm, preferably 40 mm, flow of the material of the substrate towards the main shape change is additionally assisted. The main shape change of the test surface, also at its corresponding boundary areas, is therefore adjusted via the drawing depth.

The additional shape change, on the other hand, is limited by the fact that the edge radius between the front face of the die and two latitudinal side faces of the die running parallel to the direction of the main shape change amounts to between 2 and 10 mm, preferably 5 mm. The sharp edge radius substantially prevents a flow movement towards the additional shape change, i.e., transversely to the direction of the main shape change. The main shape change as well as the additional shape change is therefore permanently predetermined in a simple manner.

In order to reduce the influence of the rectangular form of the die on the test surface, the edges between the longitudinal and latitudinal side faces of the die have an edge radius from 50 to 100 mm, preferably 70 mm.

The areas of the metallic substrate, which participate in forming during the drawing process, are preferably limited by the fact that the mould has two corrugations, running perpendicularly to the direction of the main shape change, and being arranged on both sides of the recess of the mould. The corrugations are also called draw beads. The corrugations eliminate the possibility of the substrate outside the corrugations contributing to the shape change and, thus, permit the main shape change to be substantially constant over the entire test surface.

Finally, it is advantageous if different drawing depths are permanently adjustable. Forms, which are for a specific application, can be controlled via the permanently adjustable drawing depths and reproducibly introduced into the metallic substrate, so that, for example, a drawing depth can be permanently preset in each case for the different areas of use in the construction of motor vehicles.

BRIEF DESCRIPTION OF THE DRAWINGS

There is a plurality of possibilities to refine and develop embodiments in accordance with the invention. The following drawings provide an exemplary embodiment of the invention, wherein.

DESCRIPTION

Figure 1A:
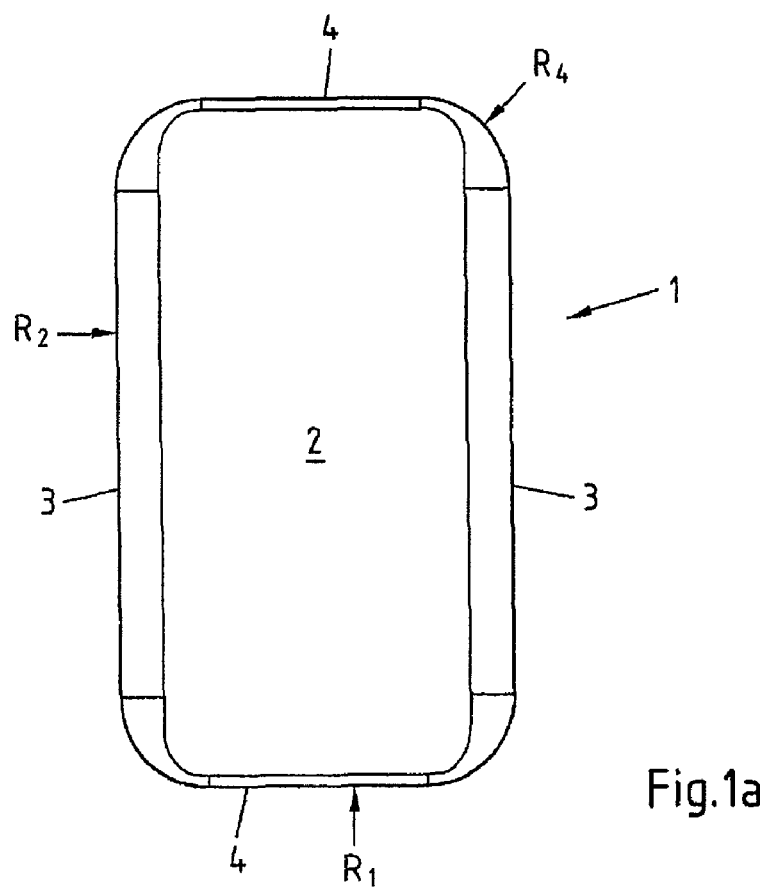
FIG. 1a) shows a plan view onto a die of an exemplary embodiment in accordance with the invention, FIG. 1b) shows the die of the exemplary embodiment from FIG. 1a) in a perspective view.

FIG. 1a) shows in plan view a die 1 of an exemplary embodiment of a device according to the invention for determining the quality of a metallic coating of a metallic substrate. The die 1 is formed in such a way that a front face 2 of the die 1 produces a test surface with a main shape change of 7% maximum when a metallic substrate is drawn. Side edges 3, 4 of the die 1 have different radii of curvature, in order to influence the flow characteristics of the material substantially towards the main shape change. The radius of the latitudinal side edges 4 in the present exemplary embodiment amounts to 5 mm, so that the material of the metallic substrate is substantially prevented from flowing beyond the edge radius and producing an additional shape change. The edge radius of the longitudinal side edges 3 of the die 1, on the other hand, is substantially wider than that of the latitudinal side edges 4, in this example 40 mm, in order to permit the material of the metallic substrate to flow beyond the longitudinal side edges 3. As a result, especially in conjunction with the radius of curvature $R_3$ of the front face 2, the direction of the main shape change of the test surface is pre-determined. During the drawing process therefore the material of the metallic substrate is extended in the entire area of the test surface by less than 7%.

The length and width of the die amount in the present example to 540 and 320 mm, respectively, in order to obtain representative results as regards testing the surface of the metallic coating. The corner radius $R_4$ between the longitudinal and latitudinal side faces of the die amounts to preferably 70 mm in order to minimize strains in the area of the test surface resulting from corners of the die 1.

Figure 1B:
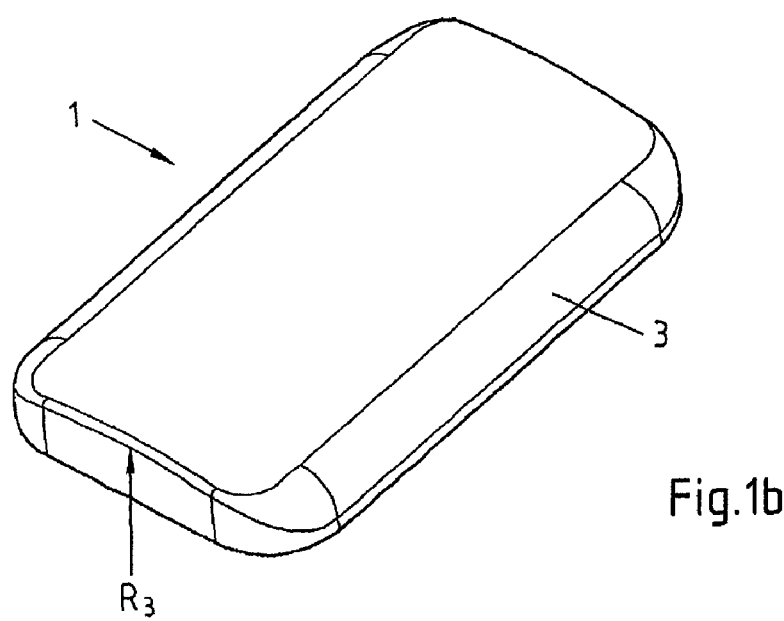

In the perspective view of the die 1 in FIG. 1b) the radius of curvature of the die 1 $R_3$, which amounts to preferably between 500 and 2000 mm, in the present example 1000 mm, changes over into a relatively wide edge radius towards the longitudinal side face 3 of the die 1. This transition positively influences the stretching characteristic of the metallic substrate, so that from the longitudinal side edges of the die 1 to the test surface 2 influences or alterations of the main shape change are minimized. The end result is that the test surface 2, which corresponds to the front face of the die 1, has a constant main shape change over substantially the entire area in one direction.

Figure 2:
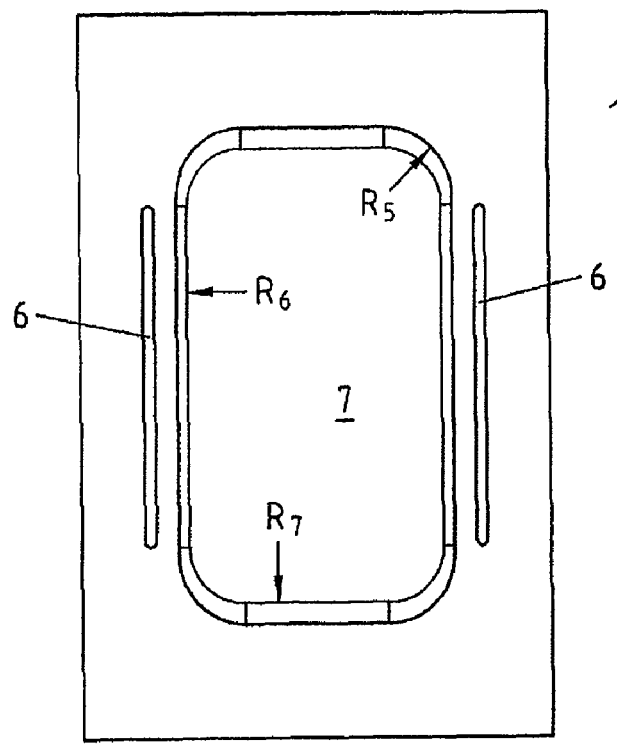
FIG. 2 shows a mould of the exemplary embodiment from FIG. 1

FIG. 2 shows in plan view a mould 5 associated with the die 1. Two corrugations 6 run parallel to a recess 7 of the mould 5, which prevents overflowing of material into the drawing area from remote areas during the drawing process. The corrugations 6 improve the homogeneity of the main shape change on the test surface, by controlling the reflow of material from remote areas of the metallic substrate. The mould 5, similar to the corner radius $R_4$ of the die 1 in FIG. 1a), has a corner radius $R_5$ of likewise preferably 70 mm. For defined adjustment of the main shape change in the area of the test surface the mould 5 has an edge radius $R_6$ along the longitudinal side of the recess 7 of 15 mm, for example. This edge radius additionally assists the effect of the corrugations 6, and permits the material of the metallic substrate to flow, particularly if the metallic substrate has a thickness from 0.3 to 1.5 mm. The edge radius $R_7$ of the transverse edge of the recess 7 can be selected as wide as 25 mm for example, since the metallic substrate should be substantially prevented from tearing along the transverse edge of the recess 7.

Figure 3:
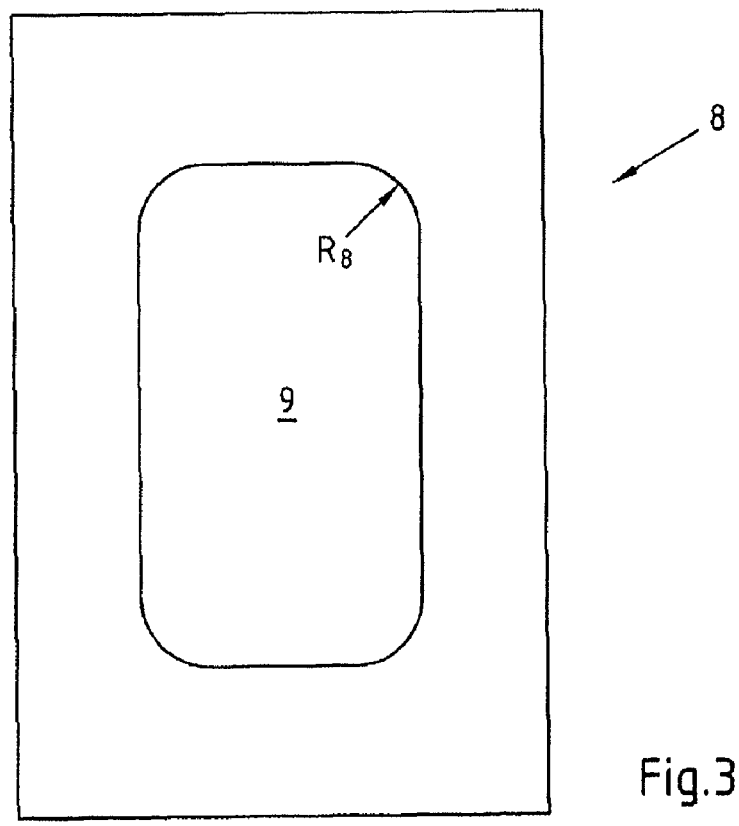
FIG. 3 shows a sheet holder of the exemplary embodiment from FIG. 1.

FIG. 3 shows a sheet holder 8 which has a recess 9 with dimensions fitting the die geometry. Also, a corner radius $R_8$ of the recess 9 is adapted to the geometry of the die 1 and likewise is preferably 70 mm.

The invention claimed is:

1. A device for determining a quality of a metallic surface of a metallic substrate, comprising:
    a mould, a sheet holder and a die configured to form a metallic substrate to produce a drawn test surface; and
    an optical and/or opto-electronic device configured to test a metallic surface of the test surface,
    wherein the die is configured to form in an area of the drawn test surface of a formed metallic substrate a main shape change that amounts to a 7% maximum change in a first direction of the metallic substrate and an additional shape change that amounts to between a −2% and +2% change, excluding a 0% change, in a second direction of the metallic substrate perpendicular to the first direction,
    wherein the die has a length of at least 400 mm, a width of at least 250 mm, and a front face with a curvature towards the main shape change with a radius of the curvature from 500 to 2000 mm.

2. The device according to claim 1, wherein an edge radius between the front face of the die and two longitudinal, length-wise, side faces of the die, running transversely to a direction of the main shape change, amounts to 20 to 80 mm.

3. The device according to claim 1, wherein an edge radius between the front face of the die and two latitudinal, width-wise, side faces of the die, running parallel to a direction of the main shape change, amounts to between 2 and 10 mm.

4. The device according to claim 1, wherein edges between longitudinal, length-wise, and latitudinal, width-wise, side faces of the die have a corner radius from 50 to 100 mm.

5. The device according to claim 1, wherein the mould has two corrugations, running transversely to a direction of the main shape change and arranged on both sides of a recess of the mould.

6. The device according to claim 1, wherein different drawing depths are permanently adjustable.

7. The device of claim 1, wherein the main shape change is defined by a curvature of the front face of the die.

8. The device of claim 3, wherein the edge radius substantially prevents a metal flow movement towards the additional shape change.

9. The device of claim 4, wherein the edge radius substantially prevents a metal flow movement towards the additional shape change.

* * * * *